United States Patent [19]

Warwick et al.

[11] Patent Number: 5,143,210
[45] Date of Patent: Sep. 1, 1992

[54] FOLDABLE PROTECTIVE PACKAGE FOR STORING, DISPENSING, AND DISPLAYING DIAGNOSTIC KIT COMPONENTS

[76] Inventors: S. John Warwick, 1141 Avenida Amantea, La Jolla, Calif. 92037; Lonna J. Williams, 13705 Stoney Gate Pl., San Diego, Calif. 92128; Robert F. Eisele, 25432 Fallen Oak, Laguna Niguel, Calif. 92677

[21] Appl. No.: 648,466

[22] Filed: Jan. 31, 1991

[51] Int. Cl.⁵ .................... B65D 69/00; B65D 5/50
[52] U.S. Cl. .................... 206/45.130; 206/45.15; 206/499; 206/569
[58] Field of Search .............. 206/438, 459, 499, 569, 206/570, 44 R, 44.11, 44.12, 45.11, 45.12, 45.13, 45.15

[56] References Cited

U.S. PATENT DOCUMENTS

| | | | |
|---|---|---|---|
| 2,062,973 | 12/1936 | Gluckstein | 206/438 X |
| 2,990,056 | 6/1961 | Gillam | 206/45.13 X |
| 3,568,883 | 3/1971 | Reynolds | 206/499 X |
| 3,580,472 | 5/1971 | Stawski | 206/499 X |
| 4,195,059 | 3/1980 | Whitcher | 206/569 X |
| 4,405,044 | 4/1983 | Flower et al. | 206/44.12 |

FOREIGN PATENT DOCUMENTS 564665 7/1975 Switzerland .................. 206/569

Primary Examiner—Bryon P. Gehman
Attorney, Agent, or Firm—Donald J. Pochopien; Paul C. Steinhardt

[57] ABSTRACT

The present invention is directed to a foldable carton for conveniently displaying the chemical reagents and for conveniently dispensing the chemically impregnated devices for use in performing diagnostic tests and provided in a diagnostic test kit format. The foldable carton of the present invention has two openings. The first opening, the cover panel, has a rack capable of containing thereon, from 1-4 containers of chemical reagents. Because the cover panel is secured to the front of the carton, when the cover panel is fully opened, so as to overlay the front wall of the carton, the chemical reagents contained thereon are forwardly displayed. Preferably, the inside face of the cover panel also contains an instruction panel for refreshing the recollection of those already familiar with the test procedure. The lower end of the front wall is provided with a dispensing flap that opens to permit the sequential withdrawal of a chemically impregnated test device that is slideably stacked within the carton. Because all reagents and devices are visible from a substantially horizontal position the carton is capable of being conveniently placed at arms length without obstructing the view of its contents.

32 Claims, 3 Drawing Sheets

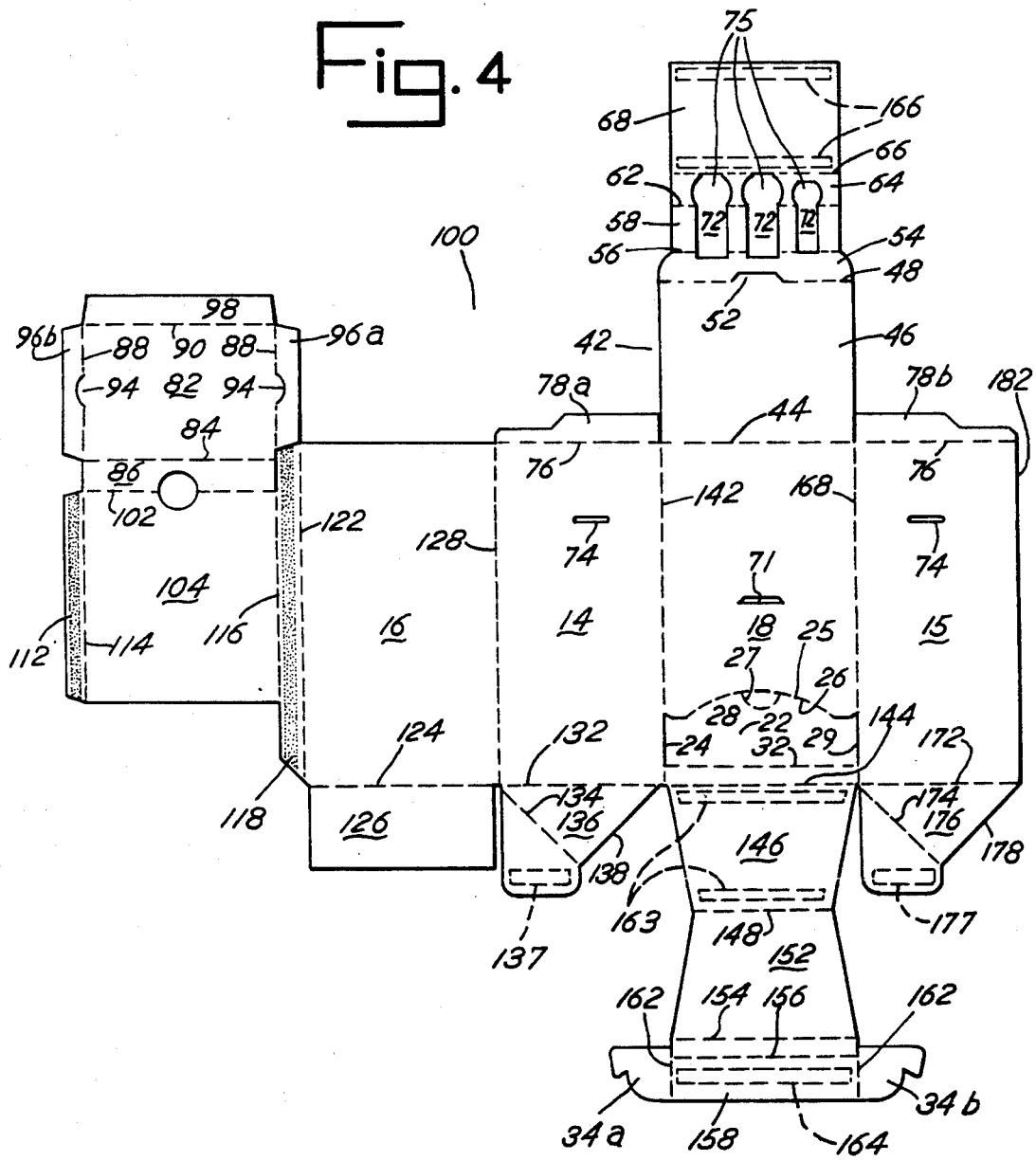

FOLDABLE PROTECTIVE PACKAGE FOR STORING, DISPENSING, AND DISPLAYING DIAGNOSTIC KIT COMPONENTS

FIELD OF THE INVENTION

This invention relates both to a foldable protective packaging sleeve or carton having multiple openings and to the blank from which it is assembled. More particularly, the present invention relates to a foldable protective package for storing, conveniently dispensing, and displaying the components of a diagnostic test kit, such as the type used in biomedical, bioveterinary, diagnostic, and research laboratories. The foldable protective package of the present invention is useful because its foldability permits the diagnostic kit manufacturer to store a greater number of the folded packages in a given volume of space, whereas its convenient dispensing, display and integrated work station features facilitate the convenient and accurate performance of diagnostic test procedures by the user.

BACKGROUND OF THE INVENTION

Every package that contains a diagnostic test kit includes as its contents an instruction pamphlet or directional insert, one or more chemical reagents and/or any required chemical impregnated devices, and occasionally, the ancillary items utilized in the performance of the diagnostic test. Upon opening the kit, the instruction pamphlet or directional insert is most prominently displayed. Often, it rests on top of the chemical reagents. Occasionally, it is positioned alongside.

The typical package currently provided by the manufacturers of diagnostic test kits is a rectangular shaped box that provides access to its contents from the top. The package opens either via a flip top or via a slip over cover of slightly greater dimensional length, width and height than the package itself. These prior art packages are of either the foldable or the rigid type. A problem with the rigid type packages is that the empty rigid packages require a large volume of storage space. Although the prior art foldable packages eliminate the storage problem associated with the rigid type packages, the prior art foldable packages require the maintenance of a second inventory of packaging inserts that have cutouts for receiving and securing the kit components during storage and shipping. Moreover, the foldable prior art packages require the physical addition of these inserts. It is an object of the present invention to eliminate both the storage and the insert related problems associated with the prior art packages for diagnostic test kits. It is also an object of the present invention to provide a fully integrated container and dispenser for chemically impregnated devices and reagents.

The packaging format for diagnostic test kits that employs the slipover cover is particularly inconvenient to use. In such a package, the side walls are all of equal height and any side views of the package's contents are obstructed. To perform the diagnostic test provided in such a package, a technologist is required to position the package on the lab bench substantially adjacent his/her body to afford a substantially vertical line of site down into the package. Although such positioning adjacent to one's person facilitates looking directly down into the package to remove and restore the kit's components, it impedes test performance. With the package immediately adjacent his person, the technologist must sidestep to one side or the other of the package to find open bench space to begin performing the assay. With a multi-component test, he is required to shuttle back and forth along the bench to remove and restore each sequential component. The alternative, which is to move the package away from one's body and thus out of the substantially vertical line of sight, is equally unappealing, since it is not only inconvenient but it can lead to reagent selection errors.

It is an object of the present invention to provide a packaging sleeve or carton for diagnostic kits which does not require a substantially vertical line of sight to view all of the components required to perform a diagnostic assay. It is a further object of the present invention to provide a package sleeve for a multi-component diagnostic kit that can be conveniently positioned directly in front of the technologist performing the diagnostic test contained therein, but which does not obstruct the working bench space immediately adjacent his person.

Every package containing a diagnostic test kit regardless of how it opens, includes a written procedure for performing the assay in either pamphlet or "directional insert" form. After having read the directional insert and having performed the diagnostic test on several occasions, the technologist becomes basically familiar with the written test procedure. However, because the result provided any diagnostic assay affects medical decisions and possibly even the life of the patient, it is essential that the diagnostic test be performed accurately and according to the manufacturer's specifications. To insure accuracy, the technologist performing the diagnostic test, will oftentimes flip through the pages of the written pamphlet or directional insert before or during the course of the test to refresh his recollection as to the sequence and/or amount of reagent to be added. This necessary procedure is both time consuming and cumbersome. It requires sidestepping to the pamphlet or directional insert, picking up the pamphlet or insert, locating the test step, and finally reading the step for which refreshment is needed. It is an object of the present invention to provide a packaging format that is capable of facilitating test performance by refreshing the recollection of the technologist, who is already familiar with the test in general without the need to resort to the pamphlet or directional insert.

SUMMARY OF THE INVENTION

The present invention encompasses a foldable protective packaging sleeve (carton) for diagnostic test kits and the blank from which the foldable carton is made. Preferably, the foldable carton and the blank from which it is made is a single piece of carton material. In its folded configuration, the foldable carton of the present invention is substantially flat and is conveniently stored, shipped and inventoried as a single item. In its unfolded (open) configuration, the carton of the present invention provides a protective carton suitable for storing and for conveniently displaying and dispensing at arms length the components of a diagnostic test kit.

In its unfolded configuration, the foldable carton of the present invention is multi-sided, having parallel front and rear walls connected along their edges by side walls. The carton is provided with a foldable bottom closure and a hinged top closure. The cover panel is hingedly connected to the upper edge of the front wall and is capable of folding back against the front wall and of engaging the front wall so as to expose the cover panel's inner face. The inner face of the cover panel is associated with a rack suitable for holding the reagents and/or disposable items that are used in performing the diagnostic test. When the cover panel is in the closed position, the carton is suited for storing and/or shipping the reagents and materials contained therein. When the cover panel is folded back and has engaged the front face so as to remain in the open position, the rack is positioned to face forward and provide an unobstructed display of the reagents and/or disposable items contained thereon. Preferably, the inner face of the cover panel also has an instruction panel thereon. More preferably, the instruction panel pictorially represents the process for performing the diagnostic test associated with the kit. Most preferably, the instruction panel also provides a pictorial key for interpreting test results.

Across the lower front wall, a continuous line of weakness defines a hinged flap and its associated opening which is of suitable size and shape for individual or in mass dispensing of a test component, such as a chemically impregnated test device. Preferably, the dispensing flap has side flaps that restrict the dispensing flap to opening an amount sufficient to dispense the test component. Preferably, the dispensing flap opens somewhat less than 90° away from the plane of the vertical front wall.

The bottom closure preferably has an upper inside flap that is hingedly connected to the front wall and that tends to lift upwardly forcing the last few components contained within the package to be dispensed toward the dispenser opening. When the dispenser flap is in the closed position, the devices in the component behind it are securely contained. When the dispenser flap is in the open position, one or more devices may be manually removed.

Because the foldable carton of the present invention displays and dispenses the components of a diagnostic test kit in a substantially horizontal direction, the kit may be utilized by a technologist at arms length which frees up the laboratory bench space adjacent his person.

In a particularly preferred embodiment, the foldable carton of the present invention includes an interior shelf that is positioned below the lid at a distance sufficient to preclude its interference with the foldable rack or its contents.

BRIEF DESCRIPTION OF THE DRAWINGS

FIG. 4 illustrates a plan view of a blank that can be assembled into a foldable one piece carton according to the present invention.

Figure 1:
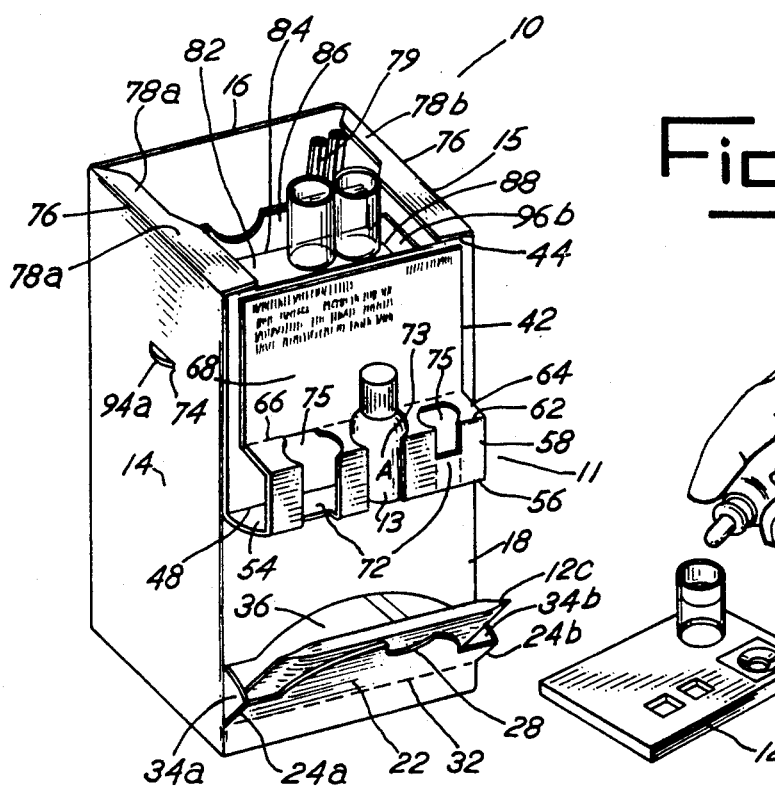
FIG. 1 illustrates a perspective view of a foldable carton according to the present invention opened into its displaying and dispensing configuration.

In the following description, spacial orienting terms such as right, left, above, below, front, back, horizontal, vertical and the like are used to describe the illustrated embodiment of the invention. These terms are used for ease of description and are not meant to be structurally limiting or requiring a particular orientation.

DETAILED DESCRIPTION OF THE INVENTION

The present invention has two aspects. In its first aspect, the present invention is directed to a foldable carton for storing, and for dispensing and displaying the components of a diagnostic test kit. In its second aspect, the present invention is directed to a foldable carton for diagnostic test kits having in combination a cover panel and rack for forwardly displaying the chemical reagents in a diagnostic test kit and a forwardly facing dispenser flap for providing convenient accessibility to chemically impregnated test devices associated with a diagnostic test kit.

In another aspect, the present invention is directed to the blank from which the foldable carton is made. In its unfolded state, the foldable carton of the present invention has four walls of sufficient length, width and height to accommodate the various components of a diagnostic test kit, such as a plurality of chemically impregnated test devices; one or more chemical reagents, typically 1–4; and optionally, one or more disposable devices utilized in obtaining or handling samples for analysis.

By the term "chemically impregnated test device" as used herein is meant a device having a membrane or surface to which one or more chemicals are adsorbed, absorbed or deposited. The "chemicals" may be inorganic chemicals, organic chemicals, biochemicals or mixtures thereof. The terms "inorganic chemicals" and "organic chemicals" are used in their ordinary chemical sense. By way of example, inorganic chemicals include buffers, metal ions, enzyme cofactors and the like. By further example, the term "organic chemicals" includes enzyme cofactors, enzyme substrates, chromogens, chromophores, pH indicators and other organic molecules such as are utilized in the generation of a detectable signal that has some relationship to the amount of analyte in a sample for analysis. The term "biochemicals" as used herein is meant those molecules found in living organisms, whether naturally occurring or synthetic, whether chemically or genetically modified, and whether soluble or immobilized. Typically, the biochemicals include: substances that are capable of binding to or reacting with the substance to be determined, such as monoclonal or polyclonal antibodies, specific binding proteins, antigens or haptens, or combinations thereof; and substances further bound to the antibodies, binding proteins, antigens, or haptens, such as homologous or heterologous oligo-or polynucleotides, enzymes, enzyme cofactors, enzyme substrates, and/or members of a binding pair (e.g., biotin-avidin, biotin-streptavidin and the like). Typically, the chemically impregnated test device is impregnated with one or more biochemicals. More typically, it is impregnated with a combination of one or more biochemicals and organic chemicals. Most typically, it is impregnated with a combination of all three types of chemicals as defined herein.

It should be pointed out that a "chemically impregnated test device" constitutes no part of this invention. Just as the garage does not define the car within it, the foldable carton of this invention does not define the device which can be contained within it. The foldable carton of this invention is capable of being used with any chemically impregnated test device.

In a diagnostic test kit, the chemically impregnated test devices can be of any size or shape. Typically, the chemically impregnated test devices are less than about 36 square inches in surface area, e.g., less than about 6 inches long×6 inches wide×½ high, for rectangular or square devices; or less than about 36 square inches and ½ inch high for a round, oval, or polygonal shaped devices.

A diagnostic test kit typically utilizes one or more chemical reagents that are not impregnated on the chemically impregnated test device. These chemical reagents include inorganic chemicals, organic chemicals, and biochemicals, as already defined herein, and combinations thereof. These chemical reagents are of the dry type, or the liquid type. The dry type includes such as, powders, beads, pellets, cakes, wafers, lyophilized material and the like. Typically, the dry type reagents require reconstitution with a liquid, such as water or buffer. The wet type reagents include solutions, concentrates, or an individual chemical in liquid form. These dry or liquid reagents are individually provided in a diagnostic kit in a respective inert container, such as an ampule, a bottle, a vial, or the like. An especially preferred container is the squeeze bottle, which is capable of dispensing a liquid reagent in a dropwise fashion.

In a diagnostic test kit, the disposable devices that are optionally included within a diagnostic test kit include sterile swabs, evacuated test tubes, capillary tubes, serum cups, pipet tips, pipettors and the like.

The foldable carton of the present invention is suitable for use with any diagnostic test kit that has chemical reagents, which are capable of being displayed, and chemically impregnated test devices which are capable of being dispensed. The foldable carton of the present invention has two openings. The first opening is at the top and it comprises a cover panel with a tuck flap. The cover panel, which is hingedly connected via a fold to the front wall of the foldable carton, is capable of swinging open approximately 270° along its hinge so as to overlay the front wall of the carton. The cover panel has a foldable rack affixed to the cover's inside face. The foldable rack typically has a base, a front and a top surface, and is of sufficient size and shape to accommodate the plurality of chemical reagents needed to perform the diagnostic test contained within the carton. All diagnostic tests have at least one chemical reagent, and typically between 1 and 4 chemical reagents.

In addition, the foldable rack may optionally hold ancillary components and/or disposable items also utilized during the course of the test. Whether the rack would hold and display these optional items is dependent upon their size, the number of reagents provided in the diagnostic test kit, and whether or not such disposable items are provided in the diagnostic test kit.

In the present invention, the foldable rack is positioned on the inside face of the cover panel such that when the cover is folded back about 270° from its closed position so as to overlay the front wall, the chemical reagents that are secured by the rack are forwardly displayed and are in a fully upright position. To retain the fully opened cover panel and its associated rack against the front wall, the cover panel preferably has a coplanar tab projecting from its outside face, which tab is capable of reversibly engaging a slot correspondingly positioned on the carton's front wall.

In the present invention, the base of the rack preferably doubles as the tuck flap for the cover panel. Because of this feature, the cover panel, its tuck flap, and its foldable rack are capable of being cut out of carton material as a single continuous piece.

Preferably, the space immediately above the rack on the inside face of the cover panel, is associated with an instruction panel. The instruction panel is for refreshing the recollection of a technologist, who is already familiar with the test procedure, as to the reagent sequence and/or amount of reagents to be added. Most preferably, the instruction panel is cut out of the carton material as a continuation of the upper surface of the foldable rack and is affixed on the inside surface of the cover panel above the rack, thereby securing both itself and the foldable rack to the cover panel's inside surface.

In combination with the open cover panel and rack for displaying chemical reagents, the foldable carton of the present invention also has a second opening, a dispenser flap. The dispenser flap has a hinge line positioned substantially at the base of the front wall and is formed out of the front via a continuous line of weakened separation, preferably, via a series of cuts and/or perforations. The series of cuts and/or perforations provide sufficient wall strength for retaining the carton's contents during shipping, but are readily severable by the ultimate user to render the dispenser flap operable. Preferably, the non-hinge sides of the flap are formed via substantial cuts in the front wall whereas the hinge of the flap is formed via a line of perforations.

The dispensing flap itself is of sufficient size and shape to permit the person who is performing the diagnostic test provided by the carton, to have ready access to one or more of the chemically impregnated test devices that are contained within the device chamber of the carton. Because the dispenser flap is located substantially at the base of the carton, the chemically impregnated test devices, which are slideably stacked in the device chamber, are gravity fed to the base of the carton where they can be serially removed via the open dispenser flap.

In its various embodiments, the foldable carton of the present invention can have from 1-3 inner chambers. However, one chamber is always the device chamber. The device chamber is of sufficient dimensions for slideably stacking a plurality of chemically impregnated test devices and their associated individual packaging (packets) if any. By the phrase "slidably stacked" as used herein is meant that the length and width of the device chamber is sufficient to allow the stacked chemically impregnated test devices and their individual packaging if any, to slide freely to the bottom of the foldable carton under the force of gravity alone.

The chemically impregnated test devices may be of the single test or the multi-test type. Preferably, each device is hermetically sealed in a packet to protect it from contamination and/or to increase its shelf life. Suitable packet materials include foil, water vapor-impermeable plastics, and the like or some combination thereof. By fixing the length and width of the packets to a greater size than the largest device to be sold, a single foldable carton that is sized to slideably stack the fixed size packet could be used for a plurality of diagnostic test kits having devices of dimensionally different sizes and shapes. Thus, by proper selection of packet size, a single foldable carton of the present invention, whether rectangular or square shaped when viewed from the top, is capable of containing and dispensing slideably square, rectangular, circular, octagonal, and polygonal shaped test devices in a variety of sizes. By way of example, and not limitation, rectangular shaped test devices are often used in chromatographic type assays; circular or polygonal devices are often used in radial immunodiffusion. However, neither the shape of the device itself nor the diagnostic test is important to the foldable carton of the present invention.

In the single chamber embodiment, the height of the foldable carton of the present invention is dependent upon a plurality of factors, such as the number and thickness of the test devices contained within the diagnostic test kit (foldable carton), the quantity and size of the chemical reagent containers that are secured to a foldable rack affixed to the cover panel, and the presence and amount of disposable items. The actual number of chemically impregnated test devices contained within the foldable carton of this invention is dependent upon the size of the carton, the thickness of the devices, their shelf life and the needs of the customer. Typically, diagnostic test kits provide from 1-500 tests/kit (carton) depending upon the test. Although the foldable carton of the present invention is capable of dispensing from 1-500 test devices merely by adjusting the carton's height, it is preferred that the foldable carton dispense from 5-100 chemically impregnated test devices. In this embodiment, a directional insert or printed pamphlet is also included. Preferably, it lay on the top of the test devices.

In another embodiment, the foldable carton of the present invention has two inner chambers, the device chamber, as already described, and optionally a disposable chamber for storing and providing any ancillary disposable items that are used in obtaining and/or handling the sample for analysis. The height of the disposables chamber varies depending upon the size of the enclosed disposable items. For tall items such as sterile culture swabs, pipettors and the like, the height of the disposables chamber is less than but substantially near the height of the foldable carton. The disposables chamber is positioned either along side or behind the device chamber. Preferably, it is positioned behind the device chamber having sufficient horizontal length and width to adequately contain all the disposable items provided. Most preferably, the disposable chamber is separated from the device chamber by an inner wall having a horizontal length substantially equal to the horizontal length of the rear wall that it substantially parallels.

Most preferably, the inner disposables chamber is cut out of the same sheet of carton material as the foldable carton, and as a continuation of one of the four walls of the foldable carton. (See e.g., FIG. 4). By providing the appropriate cuts, folds, and glue lines, the disposables chamber can be made of varying width, length and height.

In yet another embodiment, the foldable carton of the present invention has three inner chambers: the device chamber and the disposables chamber, as already described, and an upper chamber. The upper chamber substantially overlays the devices chamber such that the panel providing the tray (floor) of the upper chamber simultaneously provides a ceiling to the devices chamber. The upper chamber is suited for visually displaying a plurality of small disposable items and the package or directional insert substantially near the top of the foldable carton. Preferably, the upper chamber is separated from the disposables chamber by a flap or lip of sufficient height to prevent any small items that are in the upper chamber from inconveniently falling into the disposables chamber. (See, e.g., FIG. 3). However, the wall or lip must not be of such height as to obstruct the closure of the cover panel by contacting the rack of chemical reagents. More preferably, the panel separating the upper chamber from the device chamber has a short wall or side flap on each of its sides. Most preferably, the panel that is used to form the lips and the floor of the upper chamber is merely an extension of the panel that forms the common wall between the device chamber and disposables chamber (See FIG. 3).

The embodiment of the present invention that is selected for use depends upon a number of factors, such as the size and amount of disposables, the size of the pamphlet or directional insert and the size and number of chemical reagents and chemically impregnated test devices. However, from a convenience and inventory standpoint, the embodiment with three chambers is preferred since it can be used to store, display and dispense diagnostic test kit components whether or not the test kit also includes ancillary disposable items.

In its preferred embodiment, the foldable carton of the present invention is made from a blank (FIG. 4) that is a single piece of carton material. This reduces the costs associated with maintaining separate inventories of components of a multi-piece carton. Preferably, the one piece foldable carton of the present invention is glued and folded by a single pass of the one piece blank (FIG. 4) through a carton forming machine. The performance of all gluing and folding in a single pass reduces the manufacturing cost of the carton. Machines that feed, glue and fold blanks of carton material to form folded cartons in a single pass are well known to packaging manufacturers.

DESCRIPTION OF THE PREFERRED EMBODIMENT

As shown by FIG. 1, the foldable carton 10 is opened to its displaying and dispensing configuration which provides convenient access to chemical reagents 13, chemical test devices 12, and any supporting and equipment used with the test device. Carton 10 has upstanding side walls 14 and 15, back wall 16, and front wall 18, or top closure, a bottom closure, and a dispensing flap 22.

The dispensing flap 22 is formed in front wall 18 near the wall bottom by separating weakened line 25 which extends upwardly near sides 14 and 15 to form flap side edges 24a and 24b respectively, and transversely across front wall 18 from the uppermost extent of flap edges 24a and 24b to form flap top 26. Flap top 26 includes a grip section 28 near the midpoint of top 26. Grip section 28 is formed by removing a section 29 via the weakened lines of separation 27 bordering the middle of flap top 26. Perforated fold line 32 extends across the lowermost extent of the dispensing flap 22 (i.e., from the lower extent of flap edge 24a to opposite flap edge 24b) and provides a hinge type connection between dispensing flap 22 and the remainder of front wall 18. Dispensing sides 34 (i.e., 34a and 34b) extend into carton 10 from dispensing flap 22 (via inner dispensing flap 158; FIG. 4) and together with dispensing flap 22 form dispensing opening 36 when dispensing flap 22 is displaced away from front wall 18 by rotating about fold line 32.

The top closure of foldable carton 10 includes a cover panel 42 having an outside surface 46 and an inside surface 47, and a tuck flap 54. Cover panel 42 is a continuous extension of front wall 18. A fold line 44 extending across the top of front wall 18 allows cover panel 42 to hingedly pivot about fold line 44 between the fully open position illustrated in FIG. 1 and the closed position illustrated in FIG. 2. Cover panel 42 has a width substantially equal to that of front wall 18 and a length extending from fold line 44 to fold line 48, a distance approximately equal to the width of side walls 14 and 15. The tuck flap 54 extends from cover panel 42 along fold line 48. Tuck flap 54 secures cover panel 54 by tucking inwardly of back wall 16.

Cover panel 42 also has an inside face 47 that is associated with a rack for storing and displaying reagents and ancillary equipment. Rack 11 is composed of tuck flap 54, rack front 58, and rack top 64. Rack 11 utilizes tuck flap 54 as its rack base. Rack base 5 extends from fold line 48 to fold line 56 and is of sufficient width to support chemical reagent containers, preferably squeeze bottles, or other equipment that may be used with the chemically impregnated test device 12 during the performance of a diagnostic test. Rack base 54 decreases in width from fold line 48 to fold line 56. Rack front 58, which is an extension of rack base 54, is hingedly connected to rack base 54 along fold line 56. Rack front 58 extends from fold line 56 to fold line 62, at a height determined by the reagent containers and/or equipment to be supported on rack base 54. Rack front 58 has slots 72 to provide sufficient view of the reagent containers and their labels for easy reagent identification. To facilitate test operation, the reagent containers preferably have labels with bold sequential letters 73 (e.g., A, B, C, etc.) or numbers (1, 2, 3, etc.) that indicate the sequence of reagent addition. Rack front 58 is hingedly connected to rack top 64 along fold line 62. Rack top 64 extends from fold line 62 to fold line 66 and is dimensionally similar to rack base 54. When rack 11 is in its unfolded (open) position, rack base 54 and rack top 64 project substantially outwardly from inside face 47 for approximately the same distance such that rack front 58 is substantially parallel to inside face 47.

Rack top 64 has a plurality of spaced apart openings 75 of appropriate size and shape for insertion of reagent containers and/or equipment that are used in the performance of a diagnostic test procedure. These openings 75 provide convenient accessibility for chemical reagents or ancillary equipment when cover panel 42 is in the fully open position.

An instruction panel 68 extends from fold line 66 toward fold line 44 and fixedly overlays inside face 47. The instruction panel 68 provides sufficient instructions describing the procedure for the test contained within the package to refresh the recollection of a person already having familiarity with the test procedure. Preferably, the instruction panel 68 pictorially represents the test procedure as to the sequence and/or amount of reagents. More preferably, the instruction panel 68 also presents a pictorial key for test interpretation. When cover panel 42 is in the fully open position, instruction panel 68 provides a highly visible horizontal facing surface, displaying test instructions, test interpretation, and the like. Because both instruction panel 68 and rack 11 both provide highly visible horizontal displays of the test instructions and reagents, the carton may be placed at arms length by a technologist without loss of convenience, but with the subsequent gain of immediately available bench space in front of his person for the performance of the diagnostic test contained within the foldable carton of this invention.

Cover panel 42 is held in the fully open position (i.e., overlaying front wall 18) by tab 52 which extends coplanarly from cover panel 42 beyond fold line 48. Front wall 18 has a slot 71 that is of sufficient size to accept tab 52 and that is positioned to be at the level of fold line 48 when cover panel 42 overlies front wall 18. As illustrated in FIG. 3, tab 52 may be deflected through slot 71 when cover panel 42 is in the open position thereby retaining cover panel 42 in the open position. In the closed position, tab 52 overlies the upper edge of back wall 16. (See FIG. 2).

As shown in FIG. 1, top flaps 78a and 78b extend from fold lines 76 at the top of sides 14 and 15. Both top flaps are sized to provide support to cover panel 42 when it is in the closed position without impeding access to the interior of carton 10 when cover panel 42 is in the open position. In particular, flaps 78a and 78b become narrower adjacent the rear wall 16 to accommodate the insertion of rack 11 when cover panel 42 is in the closed position.

Tray 82 is positioned within carton 10 parallel to and below the plane of the top edges of side walls 14 and 15, front wall 18, and back wall 16. Such positioning provides convenient access to ancillary items, such as the directional insert and/or small disposable items that are stored on tray 82 when cover panel 42 is in the open position. Tray 82 extends rearwardly from front wall 18 and has a fold line 88 at the side of tray adjacent side walls 14 and 15 respectively. Tray side flaps 96 (96a and 96b) extend upwardly from tray 82 adjacent to side walls 14 and 15. Side walls 14 and 15 each have a slot 74 respectively positioned in plane with and adjacent to tray 82. Tabs 94 extend coplanarly from tray 82 and through slots 74 to provide vertical support for tray 82. Tray rear wall 86 extends upwardly from tray 82 from fold line 84. Tray rear wall 86 is substantially parallel to and spaced apart from carton rear wall 16. As shown in FIG. 3, tray front wall 98 extends upwardly from tray 82 at fold line 90 in substantially parallel contact with front wall 18. Inner partition 104, which is substantially the width of back wall 16, extends downwardly from fold line 102 at the top of tray rear wall 86 to an elevation above the lower edge of rear wall 16. Inner partition 104 also defines and separates storage chamber 108 from device chamber 112. As a result, storage chamber 108 is bounded by rear wall 16, segments of side walls 14 and 15 and inner partition 104; and the device chamber 112 is bounded by front wall 18, the remaining segments of side walls 14 and 15, and inner partition 104. In device chamber 112, front bottom flap 152 preferably lifts upwardly such that when only a few devices remain in device chamber 112, the rear end of panel 152 is hingedly tilted upward via front fold line 154 causing the few remaining devices 12 to slide forward for convenient dispensing.

Figure 2:
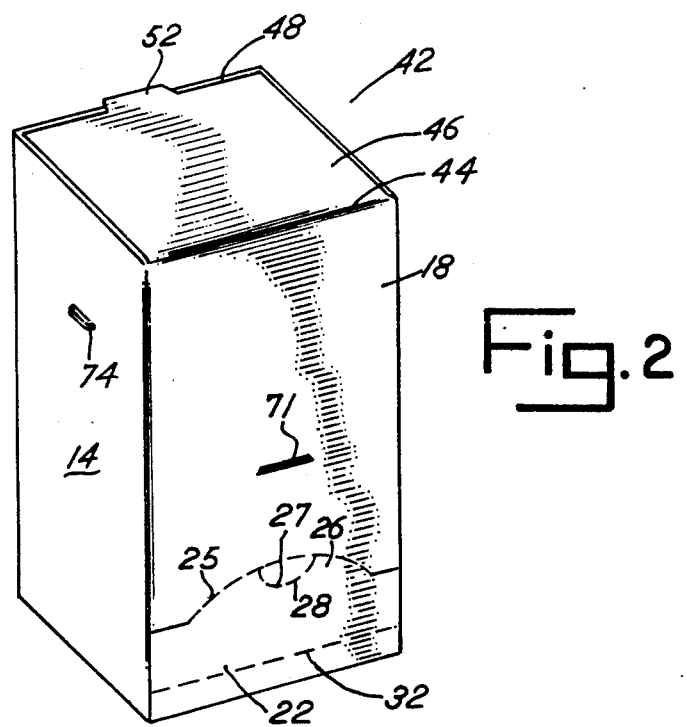
FIG. 2 illustrates a perspective view of a foldable carton according to the present invention in its closed storage configuration.
Figure 3:
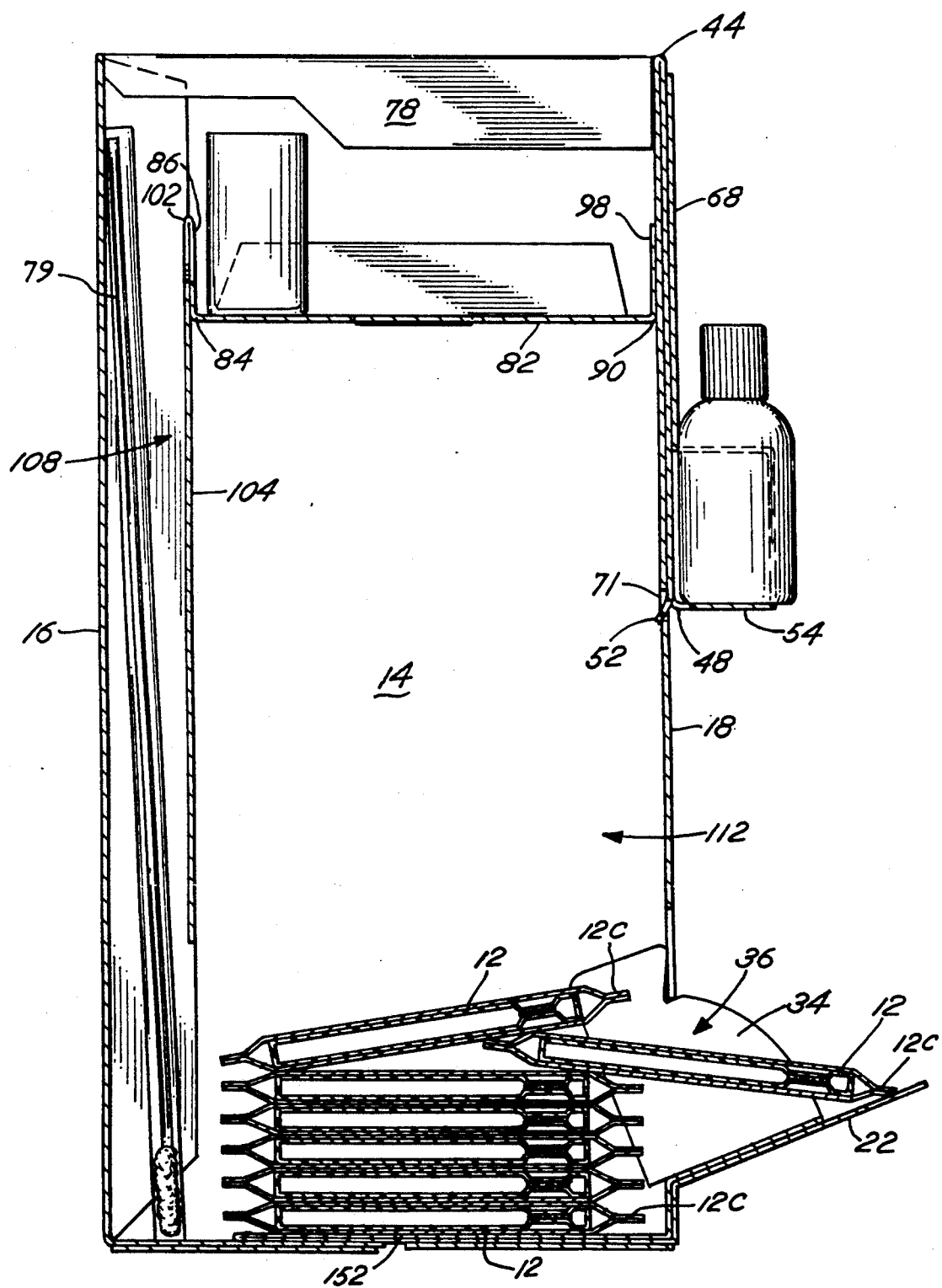
FIG. 3 is a vertical section view of the foldable carton according to the present invention as shown in FIG. 1.

As shown in FIG. 2, a dispensing flap 22 is provided on front wall 18, via a continuous line of weakened separations, i.e., a series of cuts and/or perforations, into front wall 18. The dispensing flap 22 is hingedly secured near the bottom of the front wall 18 via fold line 32, which fold line is preferably created by a series of perforations. The dispensing flap is defined at its lower end by fold line 32, and at its upper end by a continuous line of weakened separations, preferably, a series of cuts 25, extending upwardly for a short distance at or near side walls 14 and 15 respectively, and then across front wall 18. Although a dispensing flap of a particular shape is shown in FIGS. 1-4, the shape of the dispensing flap is unimportant for purposes of this invention. The dispensing flap need only be of sufficient size and shape such that when the lines of weakened separation are separated and the dispensing flap is pulled forward, the opening 36 would be sufficiently large to allow the withdrawal (dispensing) of the chemically impregnated test devices 12 that are slideably stacked within the device chamber. Preferably, the chemically impregnated devices are hermetically sealed in individual packets 12. Preferably, the opening 36 is of sufficient size to allow for the dispensing or withdrawal of more than one device at a time.

The dispensing flap 22 is preferably provided as shown in FIG. 1 with a grip edge 28. The grip edge 28 is defined by a second line of weakened separation 27 having the dimensions of a cross-section of a finger. See FIG. 2. Although the grip edge 28 could be defined by any shape of sufficient size to allow engagement with a finger, it is preferably semi-circular in shape. When the second line of weakened separation 27 is separated, grip edge 28 is formed. Thereafter, a finger is capable of frictionally engaging grip edge 28 so as to conveniently pull dispensing flap 22 forward.

Dispensing flap 22 also has dispensing sides 34 (i.e., 34a and 34b) which protrude into device chamber 112 and engage the inside face of front wall 18 to restrain the dispensing flap from opening fully. Preferably, the dispensing flap 22 is restrained from opening more than about 90°. (See FIG. 3).

A particularly preferred use for the foldable one piece carton of FIGS. 1–3 is a diagnostic test kit for detecting the presence of the micro-organism Streptococcus A via an antigen that the micro-organism produces. For this assay, the foldable carton of the present invention includes a plurality of chemically impregnated devices, chemical reagents, a directional insert, and optionally, a plurality of sterile culture swabs 79.

FIG. 4 illustrates the one piece planar blank 100 from which the one piece foldable carton 10 is assembled. The blank is cut from a continuous sheet of paperboard or the like and is provided with the appropriate folds, cuts, perforations, tabs, slots, and glue flaps, such that when it is assembled, it produces a foldable carton that is substantially flat in its folded configuration, but which is the foldable carton of FIGS. 1–3 in its various open configurations.

The blank 100 has a first side wall 15 which is connected in series with a front wall 18, a second side wall 14 and a rear wall 16. A glue flap 118 is an extension of one end of the series of walls, preferably at the end of rear wall 16, as shown in FIG. 4.

Beyond glue flap 118, the carton material extends laterally to provide inner partition 104. In the blank 100, inner wall 104 also extends upwardly to provide four sided tray 82 and via a series of folds, a flap associated with each side of the tray. Inner partition 104 also extends laterally to provide glue flap 112. Above front wall 18, the carton material extends upwardly to serially provide the top closure, the components of rack 11, and the instruction panel 68. Below front wall 18, the carton material also extends downwardly to provide in series the outer and inner bottom panels 146 and 152 and the inner dispensing flap 152 having right and left dispensing sides, 34a and 34b, that project laterally therefrom, all as a single continuous piece.

During the assembly of the foldable carton 10 of the present invention from its blank 100 as shown in FIG. 4, tray walls 96a, 96b, and 98 and glue flap 112 are folded vertically downward substantially perpendicular to the plane of the blank 100. In a series of steps, the portion of the blank that is to the left of folds 116, 122 and 128 are each sequentially folded 90° downward relative to the plane of the blank 100. Upon making the last 90° fold along fold line 128, glue flap 112 engages side wall 14 so as to form inner chamber 108. By similarly folding 90° downward the portion of the blank that is to the left of folds 142 and 168, each wall of carton 10 forms right angles relative to its immediately adjacent walls and glue flap 118 is caused to affixedly engage side wall 15 substantially near edge 182. As a result of the above series of steps, a four sided sleeve is produced having a narrow inner chamber 108 and a larger device chamber 112.

Both the bottom closure and the foldable rack 11 remain to be effected. However, it is a matter of preference as to which is to be assembled first. For purposes of this description, the assembly of rack 11 is described first. With the front wall of the four sided sleeve facing upward, instruction panel 68 is folded upward about 90° along fold line 66 so as to be substantially perpendicular to the plane of the front wall 18. Then, in a series of steps beginning at fold 62, the portion of the blank that projects outwardly from folds 62, 56, and 48 are each sequentially folded 90° downward relative to the plane of the front wall 18 and cover panel 42. Upon completion of this series of folds, foldable rack 11 is formed in its open or unfolded position and instruction panel 68 is affixed to the cover panels inside surface 47 via glue strips 166.

Bottom closure and the internal reinforcement of dispensing flap 22 is effected by the following series of steps. With the carton laying down on its rear wall, such that the front wall faces upward, both dispensing sides 34 (i.e., 34a and 34b) are folded about 90° upward along fold lines 162 so as to become perpendicular to the plane of the front wall. Thereafter, inner dispensing panel 158 is folded about 90° upward along fold line 154 so as to become substantially perpendicular to the plane of front wall 18. In a series of two folds, inner bottom panel 152 is first folded 180° downward so as both to underlay the front outer bottom panel 146 and to become affixed thereto via adhesive strips 163. Thereafter, outer bottom panel 146 is folded 90° downward along fold line 144. Upon completion of the last fold, adhesive strip 164, which is on the outside surface of inner dispensing panel 158, is caused to affixedly engage the inside surface of dispensing flap 22 so as to become bound thereto. Bottom closure is then completed by first folding outer bottom flap 126 upward 90° so as to underlay front outer bottom panel 146. Thereafter in any order, side flap 178 is folded 90° to the left so as to affixedly engage front bottom panel 146, via adhesive strip 177, and side flap 138 is folded 90° to the right so as to affixed engage rear bottom panel 126, via adhesive strip 137.

Although a particular sequence of folds is described above, the foldable carton of the present invention could be assembled, via any combination of steps, to yield the same foldable carton described above. The foldable carton as just assembled above is capable of being folded further into its substantially flat (folded) configuration for inventory, or of being maintained in its open configuration for loading, storing, and shipping.

To cause the foldable carton to go into its substantially flat (folded state) cover panel 42 must be open and tray 82 must be out of the foldable carton and substantially coplanar with inner partition 104. Then merely placing inward pressure along fold lines (lines of perforation) 134 and 174, which are on the bottom closure, causes the carton to begin to flatten with front wall edge 142 and rear wall edge 122 approaching one another. Further flattening of foldable carton 10 is accomplished by merely squeezing edges 142 and 122 generally towards one another and by squeezing rack face 58 against cover panel 42. The resulting folded carton is suitable for high density storage, inventory or shipping.

To load the foldable carton of the present invention, the open carton is first stood upwards on its bottom with the cover panel open and with tray 82 out of the carton and substantially coplanar with inner partition 10. In this configuration, a plurality of chemically impregnated test devices are slideably stacked in the device chamber. The number of devices that are stacked therein is dependent upon the height of the box. However, in practice, only kits of specific test numbers are sold. The tray 82 is then folded over so as to cover the device chamber and to permit side tabs 94 to engage and project through corresponding side slots 74. Thereafter, from about 1-4 containers of chemical reagents, the disposable items, if any, and a directional insert are added in any order.

Those skilled in the art will appreciate that modifications and variations of the resent invention are possible in light of the above descriptions. Therefore, it is understood that within the scope of the appended claims, the invention may be practiced other than described above.

What is claimed is:

1. A foldable carton for displaying the chemical reagents and for dispensing the chemically impregnated test devices in a diagnostic test kit comprising:
   a rear wall, side walls, and a front wall connected along generally parallel vertical fold lines to provide a multi-sided body that is capable of slidably stacking a plurality of chemically impregnated test devices,
   a bottom closure for said multi-sided body,
   a top closure for said multi-sided body, and
   a dispensing flap;
   said top closure comprising a cover panel having an inside face and an outside face, said cover panel being hingedly secured at a first end to the front wall along a fold line and having at its opposite end a tuck flap for tucking inwardly of the rear wall, said inside face having a rack capable of securing thereon from 1 to 4 containers of chemical reagents, said rack being positioned on the inside face, whereby when said carton is opened and the cover panel is folded forward along the fold line at said first end so as to substantially overlay a portion of the front wall, the containers of chemical reagents secured by said rack are facing forward in an upright position for convenient viewing; and
   said dispensing flap being positioned on said front wall substantially near said bottom closure, said dispensing flap being defined by a hinge line near the bottom of said front wall and by a line of weakened separation extending substantially across said front wall, said line of weakened separation defining an area having a length and height that is dimensionally greater than one of the chemically impregnated test devices to be dispensed from said carton, whereby when said line of weakened separation is separated and said dispensing flap is folded forward along its hinge line, there is created an opening capable of permitting the sequential withdrawal of the chemical impregnated test devices contained within said foldable carton.

2. The foldable carton of claim 1 wherein there are two side walls.

3. The foldable carton of claim 1 wherein said rack is a foldable rack.

4. The foldable carton of claim 3 wherein said rack has a rack base, a rack front, and a rack top.

5. The foldable carton of claim 4 wherein said rack base also functions as said tuck flap.

6. The foldable carton of claim 3 wherein said carton is capable of being folded substantially flat.

7. The foldable carton of claim 1 wherein at least one of said containers of chemical reagents is a squeeze bottle.

8. The foldable carton of claim 1 wherein said cover panel further has a coplanar tab projecting therefrom at the end associated with said tuck flap.

9. The foldable carton of claim 8 wherein said front wall further contains a slot for receiving said coplanar tab, whereby when said tab is inserted in said slot, said cover panel is restrained in said position substantially overlaying a portion of said front wall.

10. The foldable carton of claim 1 further containing from 5 to 100 chemically impregnated test devices therein.

11. The foldable carton of claim 10 wherein each of said chemically impregnated test devices is hermetically sealed in a protective packet.

12. The foldable carton of claim 11 wherein said protective packet comprises a foil, a water vapor-impermeable plastic, or a combination thereof.

13. The foldable carton of claim 1 wherein said dispensing flap further includes a grip edge.

14. The foldable carton of claim 13 wherein said grip edge is defined by a line of weakened separation defining an area about the dimension of a cross-section of a finger.

15. The foldable carton of claim 14 wherein said grip edge is substantially semi-circular.

16. The foldable carton of claim 1 wherein said line of weakened separation is a series of cuts or perforations.

17. The foldable carton of claim 15 wherein said line of weakened separation is a series of cuts.

18. The foldable carton of claim 1 wherein the inside face of said cover panel further has an instruction panel attached thereto.

19. The foldable carton of claim 18 wherein said instruction panel is positioned above said rack, whereby when said cover panel is folded forward along its fold line with the front wall so as to substantially overlap a portion of the front wall, the instruction panel faces forward and is in an upright position.

20. The foldable carton of claim 19 wherein the instruction panel pictorially represents the test procedure as to the sequence and/or amount of reagents.

21. The foldable carton of claim 20 wherein the instruction panel further includes a pictorial key for interpreting test results.

22. The foldable carton of claim 1 wherein said carton is cut from a sheet of carton material as a single piece.

23. The foldable carton of claim 1 further having three inner chambers.

24. The foldable carton of claim 23 wherein at least one of the inner chambers is capable of containing a disposable item that is used in obtaining or handling a sample for analysis.

25. The foldable carton of claim 24 wherein the disposable item is a sterile culture swab.

26. The foldable carton of claim 25 wherein the diagnostic test kit is for the detection of Streptococcus A.

27. A foldable carton for displaying chemical reagents and for dispensing the chemically impregnated test devices in a diagnostic test kit, said carton comprising:

- a rear wall, side walls, and a front wall connected along generally parallel vertical fold lines to provide a multi-sided body that is capable of slidably stacking a plurality of chemically impregnated test devices;
- a bottom closure for said multisided body;
- a top closure for said multisided body;
- a dispensing flap; and
- a rack concealed by said top closure when said top closure is in the closed position, said rack capable of securing thereon from 1 to 4 containers of chemical reagents, said rack being hingedly secured substantially near the top of said front wall along a fold line, whereby when said top closure is in the open position and said rack is folded forward along the fold line that secures said rack to said front wall, the containers of chemical reagents secured by said rack are facing forward for convenient viewing;
- said dispensing flap being positioned on said front wall substantially near said bottom closure, said dispensing flap being defined by a hinge line substantially near the bottom of the front wall and by a line of weakened separation extending substantially across said front wall, said line of weakened separation defining an area having a length and height that is dimensionally greater than one of the chemically impregnated test devices that is to be dispensed from said carton, whereby when said line of weakened separation is separated and said dispensing flap is folded outwardly along its hinge line, there is created an opening capable of permitting the sequential withdrawal of the chemically impregnated test devices contained within said foldable carton.

28. The foldable carton of claim 27 wherein when said rack is folded forward along the fold line securing said rack to said front wall, both containers of chemical reagents secured by said rack and an abbreviated set of instructions are facing forward for convenient viewing.

29. The foldable carton of claim 28 wherein said abbreviated set of instructions pictorially represents the test procedure as to the sequence and/or amount of reagents.

30. The foldable carton of claim 29 further containing chemically impregnated test devices therein, wherein each of said chemically impregnated test devices is hermetically sealed in a protective packet.

31. The foldable carton of claim 28 wherein said line of weakened separation is a series of cuts or perforations.

32. The foldable carton of claim 28 wherein said rack is retained in said forward facing position by engaging said front wall.

* * * * *